(12) United States Patent
Roobeek et al.

(10) Patent No.: US 10,465,201 B2
(45) Date of Patent: Nov. 5, 2019

(54) SOLANUM LYCOPERSICUM PLANTS WITH INCREASED FRUIT YIELD

(71) Applicant: Enza Zaden Beheer B.V., Enkhuizen (NL)

(72) Inventors: Ilja Roobeek, Dirkshorn (NL); Marieke Ykema, Harlingen (NL); Martijn Petrus van Stee, Lelystad (NL); Geert Johannes De Boer, IJmuiden (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 233 days.

(21) Appl. No.: 15/125,344

(22) PCT Filed: Mar. 13, 2015

(86) PCT No.: PCT/EP2015/055259
§ 371 (c)(1),
(2) Date: Sep. 12, 2016

(87) PCT Pub. No.: WO2015/136065
PCT Pub. Date: Sep. 17, 2015

(65) Prior Publication Data
US 2017/0107529 A1    Apr. 20, 2017

(30) Foreign Application Priority Data
Mar. 13, 2014    (NL) .................... 2012426

(51) Int. Cl.
C12N 15/82    (2006.01)
C07K 14/415    (2006.01)

(52) U.S. Cl.
CPC ........ C12N 15/8261 (2013.01); C07K 14/415 (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 6,100,449 A | 8/2000 | Fluhr et al. | |
| 9,157,093 B2 | 10/2015 | Heldens et al. | |
| 9,414,553 B2 | 8/2016 | de Haan et al. | |
| 2010/0212046 A1* | 8/2010 | Heldens ............ | C12N 15/8222 800/278 |

FOREIGN PATENT DOCUMENTS

| WO | 2009021545 A1 | 2/2009 |
|---|---|---|
| WO | 2010147467 A2 | 12/2010 |

OTHER PUBLICATIONS

Pnueli et al. (Development 125, 1979-1989 (1998)). (Year: 1998).*
Eshed et al. (Genetics 141.3 (1995): 1147-1162). (Year: 1995).*
Taoka et al. (Trends in plant science 18.5 (2013): 287-294). (Year: 2013).*
Uniprot Accession Q84XL0, dated Jun. 1, 2003. (Year: 2003).*
Uniprot Accession K4C9F3, dated Nov. 28, 2012. (Year: 2012).*
GenBank Accession AK329796, dated May 1, 2010. (Year: 2010).*
Krieger et al., "The flowering gene Single Flower Truss drives heterosis for yield in tomato", Nature Genetics, May 2010, pp. 459-463, vol. 42, No. 5.
Pnueli et al., "The Self-Pruning gene of tomato regulates vegetative to reproductive switching of sympodial meristems and is the ortholog of CEN and TFL1", Development, 1998, pp. 1979-1989, vol. 125, No. 11.
Carmel-Goren et al., "The Self-Pruning gene family in tomato", Plant Molecular Biology, 2003, pp. 1215-1222, vol. 52, No. 6.
Lifschitz et al., "The tomato FT ortholog triggers systemic signals that regulate growth and flowering and substitute for diverse environmental stimuli", PNAS, Apr. 18, 2006, pp. 6398-6403, vol. 103, No. 16.
Molinero-Rosales et al., "Single Flower Truss regulates the transition and maintenance of flowering in tomato", Planta, 2004, pp. 427-434, vol. 218.

* cited by examiner

*Primary Examiner* — Charles Logsdon
(74) *Attorney, Agent, or Firm* — The Webb Law Firm

(57) ABSTRACT

Provided herein are *Solanum lycopersicum* plants with increased fruit yield and to seeds or fruits of the present *Solanum lycopersicum* plants. Also provided herein are methods for increasing the fruit yield of *Solanum lycopersicum* plants. Further provided are fruits and seeds of the present *Solanum lycopersicum* plants. *Solanum lycopersicum* plant with increased fruit yield including the SP3D and SP gene, or at least the promoter sequence thereof, of *Solanum pennelli* or another *Solanum* species such as *Solanum neorickii, Solanum chmielewskii, Solanum chilense, Solanum parviflorum, Solanum pimpinellifolium*, and *Solanum peruvianum*.

6 Claims, 3 Drawing Sheets
Specification includes a Sequence Listing.

SOLANUM LYCOPERSICUM PLANTS WITH INCREASED FRUIT YIELD

CROSS-REFERENCE TO RELATED APPLICATIONS

This application is the United States national phase of International Application No. PCT/EP2015/055259 filed Mar. 13, 2015, and claims priority to Netherlands Patent Application No. 2012426 filed Mar. 13, 2014, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1603984_ST25.txt. The size of the text file is 18,177 bytes, and the text file was created on Aug. 18, 2016.

The present invention relates to *Solanum lycopersicum* plants with increased fruit yield and to seeds or fruits of the present *Solanum lycopersicum* plants. The present invention also relates to methods for increasing the fruit yield of *Solanum lycopersicum* plants. The present invention further relates to fruits and seeds of the present *Solanum lycopersicum* plants.

*Solanum lycopersicum* plants, also designated as *Lycopersicon lycopersicum* (L.) or *Lycopersicon esculentum* are commonly known as tomato plants. The species originated in the South American Andes and its use as food originates in Mexico, spreading throughout the world following the Spanish colonization of the Americas. Its many varieties are now widely grown, either in the field or in greenhouses in colder climates.

Tomatoes are consumed in diverse ways, including raw and as ingredient in many dishes, sauces, salads, and drinks While a tomato is botanically regarded as a fruit, it is considered a vegetable for culinary purposes. Tomatoes are rich in lycopene, which may have beneficial health effects. *Solanum lycopersicum* belongs to the nightshade family, Solanaceae. The plants typically grow to 1 to 3 meters in height and have a weak stem that often sprawls over the ground and vines of other plants. It is a perennial in its native habitat, although often grown outdoors in moderate climates as an annual. An average common tomato weighs approximately 100 grams although smaller and larger varieties are known.

Considering the economic importance of *Solanum lycopersicum* plants there is a continuing desire in the art of plant breeding to increase the fruit yield of these plants.

During the last decades, breeding was mainly focussed on yield, disease resistance, and fruit quality aspects such as uniform ripening and taste. Yield improvements have been achieved due to new production methods, improved pest management and varieties that are more suited for new production methods. New varieties with 5 or 15 fruits more per plant provided a yield increase of 2 to 4%.

Development of varieties with higher yields was hampered due to lack of knowledge regarding aspects that determine tomato yield. It was postulated that a tomato variety with two leaves between trusses instead of the conventional three leaves would shift assimilation towards the fruits, resulting in higher yield when the Leaf Area Index (LAI) is maintained.

Cultivated varieties of *Solanum lycopersicum* with two leaves between the trusses are described in WO 2009/021545. WO 2009/021545 discloses that the SP3D promoter found in a wild relative of *Solanum lycopersicum*, i.e. *Solanum pennelli*, can provide a *Solanum lycopersicum* plant with two leaves between the trusses thereby increasing the fruit yield. However, subsequent experiments have shown that two leaves between the trusses phenotype provided, for example, by introgression of the SP3D gene, or promoter, of *Solanum pennelli* into *Solanum lycopersicum* is not always stable thereby hampering fruit yield of the resulting progeny.

It is an object of the present invention, amongst other objects, to provide *Solanum lycopersicum* plants with increased fruit yield. It is further an object of the present invention to stabilise the two leaves between the trusses phenotype thereby further increasing the fruit yield of *Solanum lycopersicum* plants.

The above object, amongst other objects, is met by the present invention by providing a *Solanum lycopersicum* plant as outlined in the appended claims.

Specifically, the above object, amongst other objects, is met by *Solanum lycopersicum* plants with increased fruit yield comprising the SP3D and SP gene, or at least the promoter sequence thereof, of *Solanum pennelli*.

The present inventors surprisingly discovered that combining both the SP3D and SP gene of *Solanum pennelli* in *Solanum lycopersicum* stably provides "a two leaves between the trusses phenotype" thereby increasing the overall fruit yield of *Solanum lycopersicum* plants. With respect to increased fruit yield, up to an increase of 30% in the number of trusses was observed.

Within the context of the present invention, the term "gene" is to be understood as a locatable region of genomic sequence, corresponding to a unit of inheritance, which is associated with regulatory regions, transcribed regions, and other functional sequence regions. The present term "gene" at least denotes a genomic sequence comprising a promoter region and a transcribed or coding region.

The plant species *Solanum pennelli* is a close wild relative of tomato plant. Genes of *Solanum pennelli* can be readily introduced in *Solanum lycopersicum* plants either by traditional introgression or by modern molecular biology techniques such as by transformation. Considering the genetically close resemblance of the SP and SP3D gene of other wild relatives of the tomato plant, also SP and SP3D gene, or at least the promoters thereof, are contemplated within the context of the present invention such as *Solanum neorickii, Solanum chmielewskii, Solanum chilense, Solanum parviflorum, Solanum pimpinellifolium* and *Solanum peruvianum*.

The transcribed region of the present SP3D gene encodes a protein having an amino acid sequence with at least 90%, such as 91, 92, 93 or 94%, preferably at least 95% such as 96, 97, 98 or 99% and more preferably substantially 100% sequence identity with SEQ ID No. 1. Within the context of the present invention, sequence identity indicates the number of sequential identical amino acids in a given sequence divided by the total number of amino acids of given SEQ ID No and multiplied by 100%.

The transcribed region of the present SP gene encodes a protein having an amino acid sequence with at least 90%, such as 91, 92, 93 or 94%, preferably at least 95% such as 96, 97, 98 or 99% and more preferably substantially 100% sequence identity with SEQ ID No. 2.

It is noted that the present stable "increased fruit yield" phenotype provided by the combination of SP3D and SP gene of *Solanum pennelli* in *Solanum lycopersicum* is to be attributed to the transcriptional regulation of both genes and not the encoded protein. Specifically, at least the promoter region, i.e. the genomic region upstream of the transcribed sequence regulating transcription, is responsible for the observed effect. Formulated differently, the present trait of "increased fruit yield" is attributed to differences of regulation of the transcription of SP and SP3D in *Solanum pennelli* as compared to *Solanum lycopersicum*. Operably introducing at least the promoter sequences of both genes before the transcription sequence or cDNA sequence, especially in case of transgenic plants, will provide the present phenotype.

Accordingly, according to an especially preferred embodiment, the present invention relates to *Solanum lycopersicum* plants wherein the SP3D gene, or cDNA sequence, is under the control of the promoter sequence of SEQ ID No. 3 and/or the SP gene, or cDNA sequence, is under the control of the promoter sequence of SEQ ID No. 4.

The cDNA sequence of SP3D is provided herein as SEQ ID No. 5 and the SP cDNA sequence is provided as SEQ ID No. 6.

According to the present invention, the present *Solanum lycopersicum* plants can comprise the SP and SP3D gene of *Solanum pennelli* in either heterozygous or homozygous form, i.e. at least one allele in the present *Solanum lycopersicum* plants comprises the SP of *Solanum pennelli* and at least one allele in the present *Solanum lycopersicum* plants comprises the SP3D of *Solanum pennelli*. However, the present inventors surprisingly observed that further improvements of fruit yield, for example the number of trusses, can be obtained if one of the present promoters or genes are homozygously present, i.e. on both alleles. Optimal increase of fruit yield is obtained when both genes of *Solanum pennelli* are homozygously present.

Accordingly, according to an especially preferred embodiment, the present invention relates to *Solanum lycopersicum* plant wherein the present SP3D gene, or at least the promoter thereof, of *Solanum pennelli* is homozygously present, *Solanum lycopersicum* plant wherein the present SP gene, or at least the promoter thereof, of *Solanum pennelli* is homozygously present, or *Solanum lycopersicum* plant wherein the present SP3D gene and the present SP gene, or at least the promoter thereof, of *Solanum pennelli* are homozygously present. Within the context of the present invention, the required presence of the promoters indicates promoters operably linked to a DNA sequence encoding the respective functional SP3D and SP proteins, either by being operably linked to transcribed gene sequences or cDNA sequences.

Considering the remarkably increased of the present *Solanum lycopersicum* plant, the present invention, according to a further aspect, relates to method for providing a *Solanum lycopersicum* plant with improved yield, wherein the methods comprises introducing into the genome of a *Solanum lycopersicum* plant the present SP3D and SP3 gene, or the present promoters thereof, of *Solanum pennelli*.

According to another aspect, the present invention relates to fruits and seeds of the present *Solanum lycopersicum* plants. Inherently, the fruits and seeds of this aspect of the present invention comprise SP3D and SP gene of *Solanum pennelli* as defined above.

The present invention will be further detailed in the following example. In the example, reference is made to figures wherein:

DETAILED DESCRIPTION OF THE INVENTION

| Gene identity | Plant | Sequence type | SEQ ID No. |
| --- | --- | --- | --- |
| SP3D protein | *Solanum pennellii* | Amino acid | 1 |
| SP protein | *Solanum pennellii* | Amino acid | 2 |
| SP3D promoter | *Solanum pennellii* | Nucleic acid | 3 |
| SP promoter | *Solanum pennellii* | Nucleic acid | 4 |
| SP3D cDNA | *Solanum pennellii* | Nucleic acid | 5 |
| SP cDNA | *Solanum pennellii* | Nucleic acid | 6 |

EXAMPLE

To identify whether the SP gene might stabilize the increased fruit yield phenotype 100 introgressed plants are grown. Specifically, these plants were obtained by introgressing SP3D and SP from a *Solanum pennelli* into a *Solanum lycopersicum* plant (or *Lycopersicon esculentum*). The presence of both genes was determined by standard molecular analysis.

Figure 1:
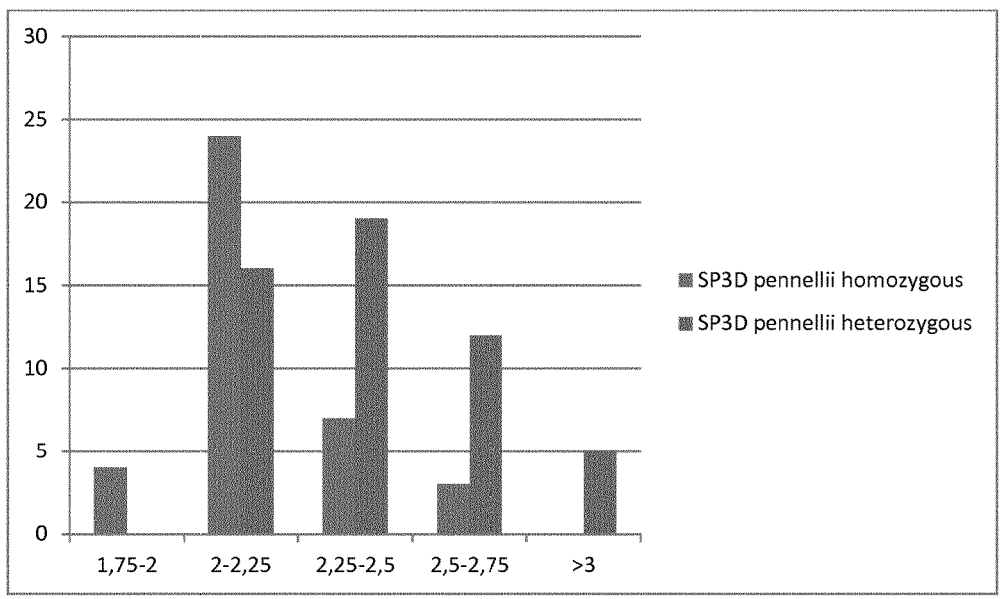
FIG. 1: shows the number of leaves between trusses of *Solanum lycopersicum* plants comprising SP3D gene of *Solanum pennelli* in the absence of the SP gene of *Solanum pennelli*.

The plants were grown under standard conditions and the number of leaves between the trusses is counted. As is shown in FIG. 1, the average amount of leaves between the trusses fluctuates between 2 and 3. Further, FIG. 1 shows that homozygous SP3D from *Solanum pennelli* resulted in less leaves between the trusses than when SP3D was in a heterozygous state.

Figure 2:
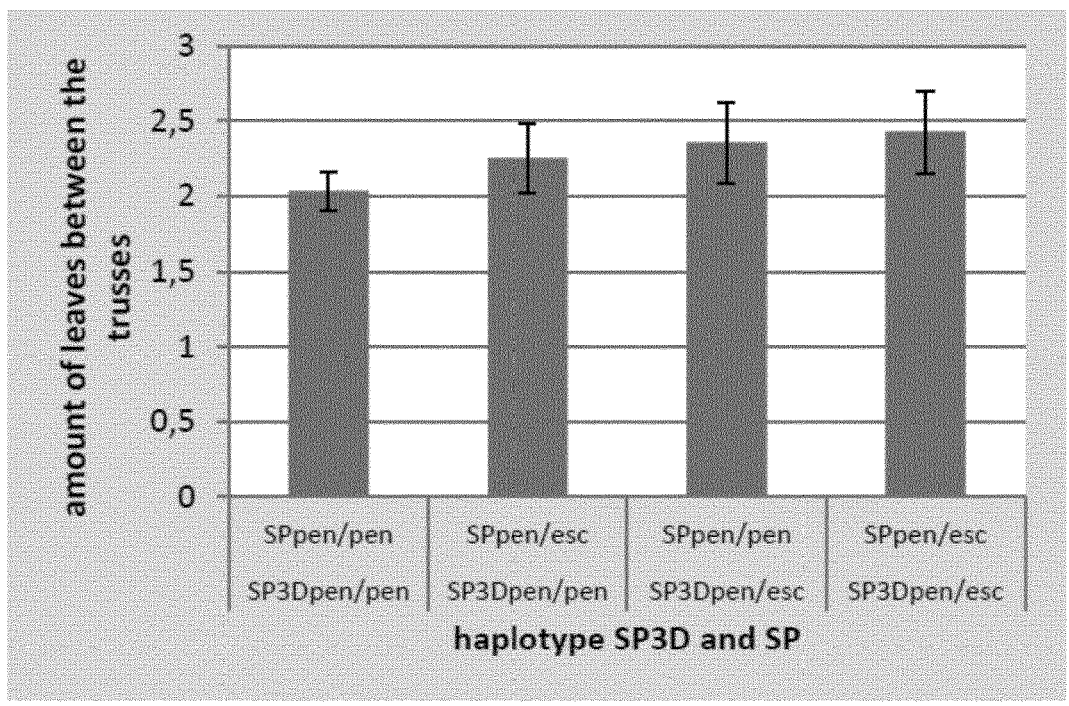
FIG. 2: shows the amount of leaves between trusses of different *Solanum lycopersicum* haplotypes. SPpen denotes the presence of the SP gene of *Solanum pennelli* and SP3Dpen the presence of the SP3D gene of *Solanum pennelli*. SPesc denotes the presence of the SP gene of *Solanum lycopersicum* and SP3Desc the presence of the SP3D gene of *Solanum lycopersicum*.

To test if homozygous *pennelli* SP ($SP^{pen/pen}$) contributes stronger to the two leaves between the truss phenotype than heterozygous *pennelli* SP ($SP^{pen/esc}$) in combination with the homozygous *pennelli* SP3D ($SP3D^{pen/pen}$) or heterozygous *pennelli* SP3D ($SP3DP^{pen/pen}$), different haplotypes that were present in the backcross family were plotted in FIG. 2 against the amount of leaves between the trusses. As can be seen in FIG. 2, when both $SP^{pen/pen}$ and $SP3D^{pen/pen}$ are present as homozygous *pennelli* in the plant the average amount of leaves between the trusses is 2 whereas all other combinations result in averages of 2.25 leaves and higher. In comparison with FIG. 1, FIG. 2 shows that the presence of *pennelli* contributes to the stability of the 2 leaves between the trusses phenotype.

To assess the fruit yield of the present plants, the number of trusses was counted in plants obtained by introgressing both *pennelli* SP3D and *pennelli* SP in a Moneyberg (*Solanum lycopersicum*) background according to the following crossing scheme:

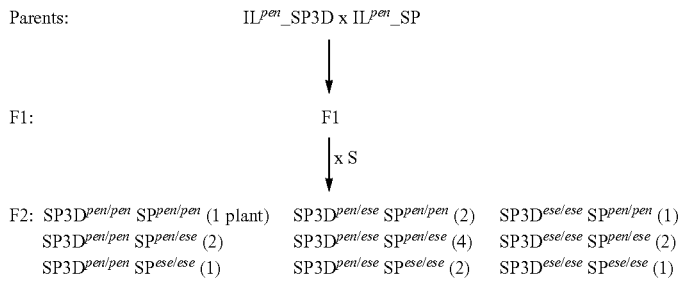

F2: SP3D$^{pen/pen}$ SP$^{pen/pen}$ (1 plant)  SP3D$^{pen/ese}$ SP$^{pen/pen}$ (2)  SP3D$^{ese/ese}$ SP$^{pen/pen}$ (1)
   SP3D$^{pen/pen}$ SP$^{pen/ese}$ (2)  SP3D$^{pen/ese}$ SP$^{pen/ese}$ (4)  SP3D$^{ese/ese}$ SP$^{pen/ese}$ (2)
   SP3D$^{pen/pen}$ SP$^{ese/ese}$ (1)  SP3D$^{pen/ese}$ SP$^{ese/ese}$ (2)  SP3D$^{ese/ese}$ SP$^{ese/ese}$ (1)

Figure 3:
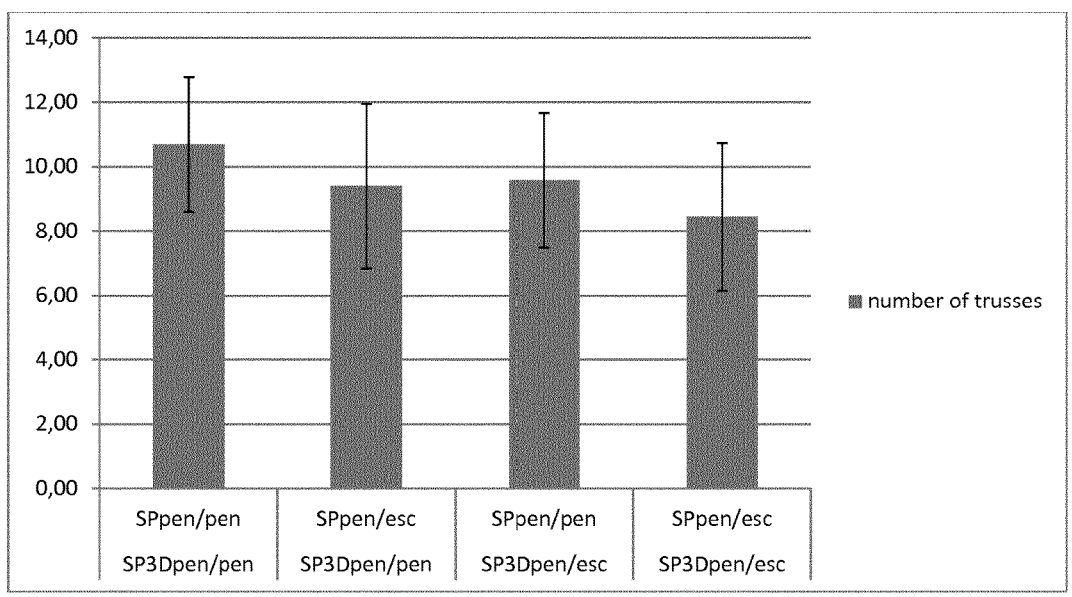
FIG. 3: shows the number of trusses of different *Solanum lycopersicum* haplotypes. SPpen denotes the presence of the SP gene of *Solanum pennelli* and SP3Dpen the presence of the SP3D gene of *Solanum pennelli*. SPesc denotes the presence of the SP gene of *Solanum lycopersicum* and SP3Desc the presence of the SP3D gene of *Solanum lycopersicum*.

The plants were grown during June to October and the number of trusses per plant was counted. FIG. 3 shows the number of trusses of 4 different genotypes. As can be clearly shown in FIG. 3, when both *pennelli* SP3D and *pennelli* SP were present homozygously, the plant has an improved amount of trusses.

The invention claimed is:

1. An isolated *Solanum lycopersicum* plant with increased fruit yield comprising in its genome a gene, operably linked to a first promoter sequence comprising the nucleotide sequence of SEQ ID NO: 3, encoding a protein having the amino acid sequence of SEQ ID NO. 1 and a gene, operably linked to a second promoter sequence comprising the nucleotide sequence of SEQ ID NO: 4, encoding a protein having the amino acid sequence of SEQ ID NO. 2, which increase fruit yield compared to a *Solanum lycopersicum* plant lacking said gene and promoter sequences, wherein said gene and promoter sequences are homozygous and are from *Solanum pennelli*.

2. A method for providing a *Solanum lycopersicum* plant with improved fruit yield comprising introducing homozygously into the genome of said *Solanum lycopersicum* plant a gene, operably linked to a first promoter sequence comprising the nucleotide sequence of SEQ ID NO: 3, encoding a protein having the amino acid sequence of SEQ ID NO. 1 and a gene, operably linked to a second promoter sequence comprising the nucleotide sequence of SEQ ID NO: 4, encoding a protein having the amino acid sequence of SEQ ID NO. 2, wherein said gene and promoter sequences are homozygous and are from *Solanum pennelli*.

3. Seeds or fruits of the plant according to claim 1, wherein the seeds of fruits comprise at least one copy of each of said genes and promoter sequences.

4. The plant according to claim 1, wherein the gene encoding the protein having the amino acid sequence of SEQ ID NO. 1 has the sequence of SEQ ID NO: 5.

5. The plant according to claim 1, wherein the gene encoding the protein having the amino acid sequence of SEQ ID NO. 2 has the sequence of SEQ ID NO: 6.

6. Seeds or fruits of the plant according to claim 4, wherein the seeds or fruits comprise at least one copy of each of said genes and promoter promoter sequences.

* * * * *

UNITED STATES PATENT AND TRADEMARK OFFICE
CERTIFICATE OF CORRECTION

PATENT NO. : 10,465,201 B2
APPLICATION NO. : 15/125344
DATED : November 5, 2019
INVENTOR(S) : Ilja Roobeek et al.

Page 1 of 1

It is certified that error appears in the above-identified patent and that said Letters Patent is hereby corrected as shown below:

In the Claims

Column 18, Line 40, Claim 3, delete "of" and insert -- or --

Column 18, Line 50, Claim 6, delete "promoter promoter" and insert -- promoter --

Signed and Sealed this
Twenty-fifth Day of February, 2020

Andrei Iancu
*Director of the United States Patent and Trademark Office*

```
                    SEQUENCE LISTING

<160> NUMBER OF SEQ ID NOS: 6

<210> SEQ ID NO 1
<211> LENGTH: 177
<212> TYPE: PRT
<213> ORGANISM: Solanum pennellii

<400> SEQUENCE: 1

Met Pro Arg Glu Arg Asp Pro Leu Val Val Gly Arg Val Val Gly Asp
1               5                   10                  15

Val Leu Asp Pro Phe Thr Arg Thr Ile Gly Leu Arg Val Ile Tyr Arg
                20                  25                  30

Asp Arg Glu Val Asn Asn Gly Cys Glu Leu Arg Pro Ser Gln Val Ile
            35                  40                  45

Asn Gln Pro Arg Val Glu Val Gly Gly Asp Asp Leu Arg Thr Phe Phe
        50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ser Ser Phe Gly Gln Glu Ile Val Ser Tyr Glu Ser Pro Arg Pro
                100                 105                 110

Ser Met Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
        130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg Ser Ala
                165                 170                 175

Asp

<210> SEQ ID NO 2
<211> LENGTH: 175
<212> TYPE: PRT
<213> ORGANISM: Solanum pennellii

<400> SEQUENCE: 2

Met Ala Ser Lys Met Cys Glu Pro Leu Val Ile Gly Arg Val Ile Gly
1               5                   10                  15

Glu Val Val Asp Tyr Phe Cys Pro Ser Val Lys Met Ser Val Val Tyr
```

```
                 20                  25                  30
Asn Asn Asn Lys His Val Tyr Asn Gly His Glu Phe Phe Pro Ser Ser
             35                  40                  45

Val Thr Ser Lys Pro Arg Val Glu Val His Gly Gly Asp Leu Arg Ser
 50                  55                  60

Phe Phe Thr Leu Ile Met Ile Asp Pro Asp Val Leu Gly Pro Ser Asp
 65                  70                  75                  80

Pro Tyr Leu Arg Glu His Leu His Trp Ile Val Thr Asp Ile Pro Gly
                 85                  90                  95

Thr Thr Asp Cys Ser Phe Gly Arg Glu Val Val Gly Tyr Glu Met Pro
                100                 105                 110

Arg Pro Asn Ile Gly Ile His Arg Phe Val Phe Leu Leu Phe Lys Gln
                115                 120                 125

Lys Lys Arg Gln Thr Ile Ser Ser Ala Pro Val Ser Arg Asp Gln Phe
            130                 135                 140

Ser Ser Arg Lys Phe Ser Glu Glu Asn Glu Leu Gly Ser Pro Val Ala
145                 150                 155                 160

Ala Val Phe Phe Asn Cys Gln Arg Glu Thr Ala Ala Arg Arg Arg
                165                 170                 175

<210> SEQ ID NO 3
<211> LENGTH: 1874
<212> TYPE: DNA
<213> ORGANISM: Solanum pennellii

<400> SEQUENCE: 3
```

| | | | | | |
|---|---|---|---|---|---|
| accatgatta | cgaattcgag | ctcggtaccc | ggggatcacc | ctctattagg | actcgtaaaa | 60 |
| agttctgagg | atacacaata | catttaaatt | aattttctta | agcattcaat | aatacattta | 120 |
| ttttgttttt | acatctttat | atgacgttac | tgatctcaga | gctagggcta | aagctctcgg | 180 |
| gcttatagtt | acaagcacta | tgaaaacatc | caaacttttg | actcttctac | tattaaacaa | 240 |
| ctttatttca | ttatattcac | ttttgtcctt | gctaataaat | caaacccttta | gtaaacgaat | 300 |
| ataaaaagaa | ccaagtaaag | acatgtgctg | ttgtcctcct | acaaattcaa | cccaacctat | 360 |
| tttagggtaa | acaaattcgg | aaaacattac | tggtgaattt | ctgacacctt | tcgtaaatta | 420 |
| aaatatattt | attcaaactc | ataaatttaa | aattataaat | tcgcgttagg | aaggaatgct | 480 |
| aagaaataga | atgagtcgaa | agagtttcaa | agaaggagag | aaccaatgtc | attatcagac | 540 |
| tgaaatgtat | gtcaaacaga | tacaatgtat | ggtaatgata | gaactaatta | actacatacc | 600 |
| actaattgca | ctatattatc | agctacccac | ctaactaact | tctatcaaaa | ttaactgtta | 660 |
| aaccaacaat | ttaacttact | cctctttttca | tattactttg | atctctattg | atctagtata | 720 |
| tcattttaga | aaactttaat | tatatgtgta | tattaatcta | atctcgttag | caatgttttg | 780 |
| gaactatgac | tattagttta | agttgttatt | taatactaaa | ggtagaaaaa | gaaaaatata | 840 |
| gcaaaatttt | cttattttca | taaattaggt | tagcaagtaa | ttattttttag | tacgaagata | 900 |
| aaagtaatat | taaaggaggg | agtaaccaat | atgtagctat | atgtcatagt | caacaaatca | 960 |
| gtagcatgga | tttctaagac | taccaactta | aagaataaga | cacgggtgat | aatttaaacc | 1020 |
| agtttaggta | ggggtaaggg | taaaatattg | gaaaaactat | ttaaatatat | aacttatttt | 1080 |
| attataatttt | ttaaaatttt | ctactatttg | aaaaaaaaat | ataacaaata | ctactttacg | 1140 |
| tgatgtatca | gtcaaataca | tcactttata | ctatatatcg | ttcagataca | tcactttatg | 1200 |
| cgatatatag | ttgtatacat | cactttacgc | gttgtaatct | gaacgtatgc | gatgtatcgg | 1260 |

```
gatattgtta ctttacgtga tgtatcggtc gaacatacat tactttacgc gatgcagaac    1320
gttgagagat gtatccaaaa tcaagacacg atgatattga gacgttttgg ggtttattcg    1380
aatttcacca aatttaagaa attttttgtaa tttgaaaaag agtccgttga ttcataacat   1440
aatgaaattt gtgtaaaatc atgaaaaata ttttaacaca aattgctatg tagaagtaat    1500
ttccacaaaa aaaaaagaa tttctaatcc gcagccgcta ccctttggct tttcctttgt     1560
caaaaaataa aatgaaaact aatcttcaaa tatgacatga ttcgattaga agaattccta    1620
gaaaacctat ggttgtaagg tgggaaaaga gaagtaatta aaaaaggcac gtactagatt    1680
ctttaggagg atatgacagc aaaaggtgct agcatgtgta tatatacaca cattctacct    1740
ctacacttgt aaaaatatgc atagcccgat aagaaactag ctagctagga gtactcttgt    1800
gttgtgtttt agcacacaaa tacacaaaag ttagccatag ctagttttta ttttgtttat    1860
cgtcaaccat cgtc                                                      1874

<210> SEQ ID NO 4
<211> LENGTH: 8081
<212> TYPE: DNA
<213> ORGANISM: Solanum pennellii

<400> SEQUENCE: 4
tgcaacatat ataattataa ttattaaaat taaggagaaa taaactactt catcgtttca     60
atttatatat tacttttaaa tttcaagatt taagcaagtt attttttcttt ttatatattt   120 ttaaattact tatcattatg aattactata ttttttgacac aattcttctg tgtatatata   180
tgtgtgtgta tataatcgaa attaaattat ttgattctat aaattgggat aatataaaaa    240
ggaatatgga gaaaagggta aattgagaat tctattaata gtatgcttct tctttctact    300
actaggagta ggagttataa agctgcataa attgagtttc ttttttgttg atatgacttg    360
accttggcta ccaccatcaa ttgttaacag gctggtggtg gactactact ctcccttat    420 actcctacct agcctaccat ttaatttatt taatttggtt atcactcaac tttttttatt   480
ttattaacaa aaaaagaaaa attattagga aaagttgcaa cttttttgtta ccttaaaatac  540 aaaagtttgt ttgatgcttt aagtagcttc agaatgtcca agatggtatc tgcaaattcc   600
atctgatttt ccttttaggg ggttgtgtgt ttctcactta cctctgatgt ttgattatga   660
taattaaaaa aaaaattgtc ataaaatatt tgtgtgtaat ttaggttgca cagagggatc   720
ttggggtgtg gggttgggtg gtattagatg agtaatgtga aatgtattta tgaaaaaaaa   780
taaaaaattt agagtatgac catctcaatt cttattttt tacaatattg attcttcata    840
ttacatctca aatcttattt tttacaatat tgattctgca tattaaattc cctacgctgg   900
aacgtccaaa aatctcacaa tcacatgaag aaggtatgaa tggtctcctt attatagtcg   960
tatgcttctt tctttgcact taattaatat gttgttgagc tgataaatat gatactaata  1020
aaaagtattt tgtgtgtaat ttttgtcaat attttattca ttactaacta tcaccgtgac  1080
taactatctc tatcctcaca attaccctac taccattatt gtcatcaacg actaatcatc  1140
actatcaacc atcattgtca ttataatcac cattattgtt aatcactata tattatcagt  1200
tgctacgata tattttacgt ttattataat tatatctact gtcaccattg atgaaatagg  1260
aatagattga agtaaatata actagtgagt tagttagtct tttatcaagt tagtcagaaa  1320
ttagttattg gcatcttaac ttgcacatga taggtagtta gatataatta gtcacattat  1380
aaatatgctg taacaaacca atattgtaat tcaatttttct gcaatataca atacacagtt  1440
ttctcaatga gttttcttct tcttcatctt ctccatcttc tattctcttc atcttcatag   1500
```

```
atttagttac aaattttcaa taattcaaca tggtatcaga gcagaaactc atgattatga    1560
gttagatcct gcataatctt tgtagaattc tttaattttg ttgagatttt ctgttgattt    1620
gatctttaac aatatctaaa actgacattg atcataatca tccactttat cttcatcctt    1680
cagaaactac tggagttgct atcatctcaa tacgattgac aggatcagaa aactattcat    1740
tatggagtcg agcgatgcga atccagctgt taggaaagaa caagttggga ttgatcgatg    1800
gtaccttgag tgtggacagt tttgataaag aacttagtca tcaatggaat cgttgcaatg    1860
caatcgtagt gggatggatt atgagttcag taggaaagga gttacttaca ggaatattat    1920
atgccaaaga tgccagatca gtctgggaag atctaagaga gcgttttgac aaggtcaatg    1980
catcaaggat ctatcagttg cacaaaggaa tagcaacaat tacgcaaggt tcagataata    2040
tttcaatcta tttctcaaaa cttcgagatt tatgggtcga attcgacagt atggttccca    2100
atccttgtga ttgtcctaaa tccaaggatt tgttgcaca tatggagagt caaaagctaa    2160
tgcaattttt aatgggactt aatgaatcat atgatcatgc gagaagccaa attctaatga    2220
ctactcctac acctagtgtc aacaaagcct attctatgct tattgaaagg gaaagccaaa    2280
gaactatggc aaacacatct atcatgggac aagaaaatga agtagctgca cttcttgcta    2340
gtaagaaaga tggttatcag aaatcacaaa gaaattggga gttacaatgt gattactgtc    2400
atatgaaggg acatacgaag ctcaattgtt atcgactaat aggatattct caaaattatt    2460
tcaaaaacaa gaagaaagta ggacaagaaa atacagcata taatgtacac acagagagag    2520
atgcaaagat gacagagaac agttctaatg ataggaatat gcagagagca ccaactttta    2580
acaatggaca gtatgatcag atagtaaaat tgctagatga agaaaaatct catgccaata    2640
tggtgaatat ggcaggtatg atccattctt ttatggctaa tatagaacaa gacaaatgga    2700
taattgatac agggggcatcc aatcacatga ctgcatattt ggataatttg tctgacgtta    2760
ggattattaa tccagagaaa tgtgagaagg tttatttgcc aaatggagga gtgactttag    2820
tttcacgcat aggaaaatac aagcttacaa atacagatga aatcagcaat gtgtttttta    2880
ttccagattt taagtataac cttctatcag tgtcaaaact aactagggaa ttgagttgct    2940
ttgtatcctt ttatcctgat ttctgtttgt tccaggacct ttccactggg aaagtgaagg    3000
ggattggtag agagaaggat gggctttatc tcatgaactc taagaattcc acaaaaagag    3060
cagttgcagg taatacaatc acaaaaatgg agtgtgctga tagtttgaat aaaactgaca    3120
aattgctgtg gcataaaaga ccgggacatg cttccagcac aactatgaag gagatacttg    3180
gttgcaaatt aggtgattgt aaagatgtta ttgagaatta taatgtgtgc cccttagcta    3240
ggcataccag attagctttt cataatagtg agttaaaatc atgtaaggct ttccaactat    3300
tgcatatgga tgtatgtgga cctcataaca ttcctacttt tgatgaaat aaatacttcc    3360 ttactgttgt tgatgatttc actcgtgtca cgtgggtatt tcttatgaag tttaaaaatg    3420
atgtattgcc tatttaaga tctttcttca agatgctaca aacacaattc aaggctgaga    3480
ttcaaactgt gagatcagac aatggtgggg agttcgtgaa ttttgattta gctgaatggt    3540
ttaaagattt agggattgtt caccagaaaa cttgtgcata tacccctcag cagaatggag    3600
ttgctgagat gaaacataga cactagtag agtttgcaag agctctaaag tttcaaggtc    3660
atattcctaa taattttgg ggtaattgtg ttcttacatc tgcatatatt attaacaggc    3720
tgccatcagc tgtattaaaa ggaaaatctc cttatgaaat gttgttcaag agaaagcctc    3780
gtttagatca tcttagggta cttggatgtt tgtgttatgc aagtgattta ccaaaaggtg    3840
```

-continued

```
ataagtttga aagtagagct gtacaagctg ttttcatggg gtattcatct gtctctaaat    3900
gttatattct tttcgacata gcaaaacgta agttttttgt aaatagggat gtagtgttca    3960
gagagtttac atttccttt caacattctt ctgcatctgg tgatgattgt tcttttgatt    4020
atgattactc atgtgattca tcctattatg atatcaatcc tgatatacat gtttgtccta    4080
cttcacctcc tcttggatct gattcatatt ttgatgcaca tatggtgcct acttcagtag    4140
aggttgcttt aatggaggtt cctgttgtaa cttctattga tagttcttct aatcttccaa    4200
gaaggtctca aagagtatcc tctagacctc tttggatgac agattatgtg actgcaccat    4260
ctgggaattc tgtgcaatat cccatacaag actatatgtc ctatataggc ttgtcagctt    4320
cacactatag ttttttgagc atgctgaaca ctgtggttga accatctact tatcaacagg    4380
cttcacaaga ccctcgttgg atagatgcta tgaatgctga gatacaagcc ttgcaggata    4440
atcatacttg ggactcttta cctccccgga acatcctat aggttgtaaa tgggtatata    4500
aagttaaact tcaggccaat ggtgacatag agaggtttaa ggctcgtctt gtggcaaaag    4560
ggtataatca acggaaggt cttgattaca atgagacttt ttctccagtt gtcaaaattg    4620
ctactgcgag aactgtatta tctatagctg ctcaacatga ctggcatatt catcaacttg    4680
atgtctataa tgcatttctt caaggggatc ttcatgatga agtatatatg cagttgccac    4740
aaggttttcc aagtcagggg gagtctatag tttgtagact tgttaaatcc ttgtatggga    4800
tcaagcaagc aagtagacaa tggaatgtga agttaacgga agccttgctg cattctcaat    4860
ttcaatagag caaattggat cattcattgt tcataaaaag agaaggtaaa agcactgtga    4920
tcatccttat ttatgtggat gatatgttgg taacagggaa tgatttggag ttgatcagaa    4980
ggaccaagga agaattacac aaagcattca agatcaaaga tttaggaaat ttgaaatatt    5040
ttcttggtat ggagtttagc aggtcaaaga aaggaatatt aatcaaccaa agaaaatacg    5100
cattagagat aatctcagaa acaggactag gggagctaa acctgcatgg acaccattag    5160
aaataaatga aagttgaca gcgattgagt tagataaacct aactggaaag gaagatgatg    5220
acatgttaga agatgtagga cagtataaaa gaggcattgg aagattattg tatttgactt    5280
taacaagacc tgatatagca ttctcagtac aaactcttag tcaattttta cagcagccaa    5340
agaaatctca ttgggatgca gcaatgagga taatcagata tgtcaagaga cagccaggtc    5400
ttggaatttt tgatgagtagt taataaatct aataatatgg tagtatactg tgattcagat    5460
tgggcatcat gcccaaatac aagaaggtcg gtatcaggtt ttttggtcaa gtatggagac    5520
tcattgattt cttggaagtc gaagaaacag accactgtgt ctaggagttc agcagaggct    5580
gaatacagaa gtatgggaag tgcagtagct gagatagtat ggttgacaac tctaatgaaa    5640
gaattggagg ctggaattga gatacctgtt aaagtttaca gtgacagcaa agctgcattg    5700
caaattgctg caaaccctgt gtttcacgag agaacaaaac acatagaaat tgattgtcat    5760
tttattaggc agaaaattca agaagggtta gtagagactg aacatgttgg aactaaggat    5820
caaacagaag ccatattgac aaaaggactt ccaagagtac aacatgaata tttagttggc    5880
aagctgggga tgcttaacat ttttgcacct gccagcttga ggggagtga tgaaataggga    5940
ataggttgaa gtaaatataa ttagtgagtt agttagtctt ttatcaagtt agttagaaat    6000
tagttattag catcttaact tgcacatgat aggtagttag atataattag tcacattata    6060
aatatgctgt aacaaaccaa tattgtaatt caattttctg caatatacaa tacacagttt    6120
tctcaatgat ttttcttct tcttcatctt cttcatcttc tattctcttc atcttcatag    6180
atttagttac agattttcaa taattcaaca accatcacca tactcacaat tactaccacc    6240
```

| | | | | |
|---|---|---|---|---|
| tccaccatca | ctatcaacca | ctacaatcct | tgcgatcaat | ctctactaca aaccaatgaa | 6300 |
| ccattttcat | tatcataact | agcacagcta | ctatcatcaa | cacatcatca attaccatat | 6360 |
| atattcttca | cccatcgctg | ttaatatcac | taactattaa | tatcaatcaa cttcactagg | 6420 |
| acaatcacca | tcaccactat | taaatgtcat | catcacacca | gtcattacaa actaatagt | 6480 |
| ctccaacatt | accagtaatc | actaacaacg | accattatta | caaacaatct ctactcattt | 6540 |
| acttttattc | aaatatttat | ttagacaaaa | ctgattttag | taaaacaaat gagatcaatc | 6600 |
| tttttctcgt | gattaatttt | taagttggaa | ttagttccaa | aatacattta atatagacaa | 6660 |
| atatgatatt | ccttccgtcc | cattttatgt | aaaaagaaac | gtttcatttt cttatatggt | 6720 |
| aagtatttaa | agatataatt | tctctttttt | acctttattg | atcttaattt tctaatacat | 6780 |
| ttatgaggag | agagaaaaat | gagttacttt | tttgaaggac | aatttgataa acatttcaaa | 6840 |
| gtcttcatta | tttcttaaac | ttcgtagcgg | gtcaaatatt | ttcacataaa atgggacgga | 6900 |
| gggagtaaaa | catatgaagc | acaccctta | tttaaaatag | tgtaggtact atctaaaagt | 6960 |
| ggaagtaaat | tatttgtttc | cccaaaatta | aattttaccc | ttggacagca attcctgttc | 7020 |
| aagggttaat | tgtataggga | catacatttt | cttctaatag | tccagcgtag tttggttttc | 7080 |
| gatatgtgga | aaattatctc | gacataaaat | gttacagtaa | ctaattagta caatatttag | 7140 |
| tttgtattta | ccattacctt | tagctccaca | ttcacataaa | ttggtagtac aacatttaat | 7200 |
| cttctaattt | gtactataac | attttcattt | atataaagta | tggtttctat cttcaccatt | 7260 |
| agcgtaacgt | tcgagtagag | atatacatat | ttattattat | aatatacgat tacaaatgcc | 7320 |
| aaagatggct | aattttgttt | tgagagacta | ctgcattatc | taactttttt cagagacatg | 7380 |
| tataagatta | agtctattgc | caattctcaa | atattactct | tttttactta ttgtggttat | 7440 |
| ttatacatat | taagtgaact | ttcttttaag | acaaaaatgt | gaaagaaatg aatttcaaat | 7500 |
| ttgattcaat | tccataaaat | agctcaaatc | ggaggaggaa | ttaatattca agtcttataa | 7560 |
| ggaaactatt | catcgatcat | gattattttt | ccatgttaaa | ttgattaaat ctttttcat | 7620 |
| tcttcaacat | acctaatctt | ctaccctaca | acaagctttc | acctttcata gtatttatat | 7680 |
| agactatata | ttcgtataaa | atattttct | tcaagtcgaa | tacacatgat cttttaaga | 7740 |
| tagagggagt | atttttaaa | aaaaaaataa | tggggcaaac | gcaaataaaa tagaacacat | 7800 |
| atatattctt | tctctagctg | ctaattaagc | tatgactttta | taattttgta gcacgagaag | 7860 |
| agaataaccct | ttttgtgctt | ttcatttctt | taatttggtt | ccccattttt tgaactatca | 7920 |
| atattttagt | ccctatccca | tctgactctc | taatgatctt | agggccacta taaatattgg | 7980 |
| tattttgctc | ttcttttctc | catcaaaaaa | caactacaac | tctttaaata gatttttgttt | 8040 |
| tgtgtcttat | aattaattaa | taattaactc | taaatatata | t | 8081 |

<210> SEQ ID NO 5
<211> LENGTH: 534
<212> TYPE: DNA
<213> ORGANISM: Solanum pennellii

<400> SEQUENCE: 5

| | | | | |
|---|---|---|---|---|
| atgcctagag | aacgtgatcc | tcttgttgtt | ggtcgtgtgg | tagggatgt attggaccct | 60 |
| ttcacaagaa | ctattggcct | aagagttata | tatagagata | gagaagttaa taatggatgc | 120 |
| gagcttaggc | cttcccaagt | tattaaccag | ccaaggggttg | aagttggagg agatgaccta | 180 |
| cgtacctttt | tcactttggt | tatggtggac | cctgatgctc | caagtccgag tgatccaaat | 240 |

```
ctgagagaat accttcactg gttggtcacc gatattccag ctaccacagg ttcaagtttt      300
gggcaagaaa tagtgagcta tgaaagtcca agaccatcaa tgggaataca tcgatttgta      360
tttgtattat tcagacaatt aggtcggcaa acagtgtatg ctccaggatg gcgtcagaat      420
ttcaacacaa gagattttgc agaactttat aatcttggtt tacctgttgc tgctgtctat      480
tttaattgtc aaagagagag tggcagtggt ggacgtagaa gatctgctga ttga            534

<210> SEQ ID NO 6
<211> LENGTH: 528
<212> TYPE: DNA
<213> ORGANISM: Solanum pennellii

<400> SEQUENCE: 6
atggcttcca aaatgtgtga accccttgtg attggtagag tgattggtga agttgttgat       60
tatttctgtc caagtgttaa gatgtctgtt gtttataaca acaacaaaca tgtctataat      120
ggacatgaat tctttccttc ctcagtaact tctaaaccta gggttgaagt tcatggtggt      180
gatctcagat ccttcttcac actgatcatg atagatccag atgttcttgg tcctagtgat      240
ccatatctca gggaacatct acactggatt gtcacagaca ttccaggcac tacagattgc      300
tcttttggaa gagaagtggt tgggtatgaa atgccaaggc caaatattgg aatccacagg      360
tttgtatttt tgctgtttaa gcagaagaaa aggcaaacaa tatcgagtgc accagtgtcc      420
agagatcaat ttagtagtag aaaattttca gaagaaaatg aacttggctc accagttgct      480
gctgttttct tcaattgtca gagggaaact gccgctagaa ggcgttga                   528
```